United States Patent [19]

Wood

[11] Patent Number: 5,286,810

[45] Date of Patent: Feb. 15, 1994

[54] SALT OF POLYMER FROM MALEIC ACID, POLYAMIND AND AMMONIA

[75] Inventor: Louis L. Wood, Rockville, Md.

[73] Assignee: SRCHEM Incorporated, Elkridge, Md.

[21] Appl. No.: 44,900

[22] Filed: Apr. 7, 1993

Related U.S. Application Data

[63] Continuation-in-part of Ser. No. 926,242, Aug. 7, 1992, abandoned.

[51] Int. Cl.$^5$ ............................................. C08G 69/48
[52] U.S. Cl. .................... 525/421; 210/698; 433/216; 525/422; 525/435; 528/332; 528/335; 528/345; 528/363
[58] Field of Search ................ 525/421, 435, 422; 528/345, 332, 335, 363

[56] References Cited

U.S. PATENT DOCUMENTS

| | | | |
|---|---|---|---|
| 3,351,520 | 11/1967 | Spicer et al. | 525/421 |
| 3,846,380 | 11/1974 | Fijimoto et al. | 260/78 A |
| 4,363,797 | 12/1982 | Jacquet et al. | 424/70 |
| 4,585,855 | 4/1986 | Gaku et al. | 525/421 |
| 4,839,461 | 1/1989 | Boehmke | 523/363 |
| 5,057,597 | 10/1991 | Koskan | 528/328 |
| 5,152,902 | 10/1992 | Koskan et al. | 210/698 |

OTHER PUBLICATIONS

Harada, K. et al. Thermal polycondensation of free amino acids with polyphosphoric acid. Chemical Abstracts vol. 63, Jun. 1965, 685e.

Stinson, S. Polyaspartic acid process developed. Chemical and Engineering News, Jul. 20, 1992, p. 21.

Sarig S. et al. The use of polymers for retardation of scale form. National Coun. Res. Dev. (Rep.) (Isr.) 150–157, Jun. 1977.

Kovacs et al. Chemical Studies of polyaspartic acids. Journal of Organic Chemistry vol. 25, pp. 1084–1091, Jun. 1961.

*Primary Examiner*—Harold D. Anderson
*Attorney, Agent, or Firm*—William S. Ramsey

[57] ABSTRACT

Higher molecular weight copolymers of polyaspartic acid which are suitable for the inhibition of scale deposition may be obtained by reacting maleic acid and ammonia in a stoichiometric excess, with a diamine or a triamine, at 120°–350° C., preferably 180°–300° C., and then converting the copolymer of polysuccinimide formed to a salt of a copolymer of polyaspartic acid by hydrolysis with a hydroxide.

4 Claims, No Drawings

SALT OF POLYMER FROM MALEIC ACID, POLYAMIND AND AMMONIA

This application is a continuation-in-part, of application Ser. No. 7/926,242, filed Aug. 7, 1992, now abandoned.

FIELD OF THE INVENTION

This invention relates to a process for the production of copolymers of polysuccinimide, their conversion to salts of copolymers of polyaspartic acid and the use of these materials.

BACKGROUND OF THE INVENTION

The salts of polyaspartic acid have been used for fertilizers and scale inhibition agents. They are particularly useful for the prevention of scale deposition in boiler water, reverse osmosis membranes, detergents and as inhibitors of dental tartar and plaque formation (tartar barrier agents). These materials are readily biodegradable. Economic methods of production of polyaspartic acid having a higher molecular weight is desirable to provide materials having a greater retention on the object wherein inhibition of scale deposition is desired, and to provide greater stability to biodegradation in addition to their intrinsic value for the prevention of scale deposition in boiler water, reverse osmosis membranes, detergents and as inhibitors of dental tartar and plaque formation (tartar barrier agents).

Highly functionalized, yet readily biodegradable materials, which function as inhibitors of scale deposition are desirable for use as fertilizers, in detergents, in water treatment, and in control of tartar.

The problem of obtaining higher molecular weight polymers of amino acids has been given a great deal of thought due to the rapid degradation of these polymers, especially in the mouth. A major drawback to the use of such polymers as antitartar agents is the lifetime that such polymers have in the mouth. Achieving a means by which a higher molecular weight agent can be obtained is desirable from both an economic and a use standpoint.

DESCRIPTION OF RELATED ART

A number of methods of preparation of polyaspartic acid are disclosed in the literature and other patents, however, no mention is made of methods of preparation of copolymers of polyaspartic acid.

U.S. Pat. No. 4,839,461 discloses a method for making polyaspartic acid from maleic acid and ammonia by reacting these constituents in a 1:1-1.5 molar ratio by raising the temperature to 120°-150° C. over a period of 4-6 hours and maintaining it for 0-2 hours. It is further disclosed that temperatures above 140° C. result in elimination of $CO_2$, thus teaching degradation of the material. The molecular weight range obtained by this method was said to be 1,000-4,000 with a cluster at 1,800-2,000. It is further disclosed that this material is useful in the prevention of tarnishing on glass and porcelain articles. Although not stated, it is known that this action would occur as a result of the inhibition of divalent metal ion salt deposition.

Harada, et al (Thermal polycondensation of free amino acids with polyphosphoric acid. Origins Prebiol. systems Their Mol Matrices, Proc. Conf., Wakulla Springs, Fla., 289, 1963) obtained polysuccinimide from aspartic acid and phosphoric acid at temperatures over 100° C. over a time period of 50-250 hrs, but required temperatures over 170° without phosphoric acid being present. Conventional alkaline hydrolysis provided polyaspartic acid. No molecular weight range was given.

Sodium polyaspartate of 6,000 molecular weight (MW) was used in the prevention of boiler scale by changing the crystal structure of calcium salts resulting in the formation of a soft scale (Sarig et al, The use of polymers for retardation of scale formation. Natl Counc Res Dev [Rep] (Isr.), 150, 1977). Polyaspartic acid was found to be superior to polyglutamate, MW 14,400, polyvinyl sulfonate, MW 5300, and polyacrylic acid, MW 6,000, in that it gave 66% retardation of total scale and 90% retardation of calcium sulfate scale. In addition, the scale formed in the presence of polyaspartate was softer than that produced in the presence of polyacrylate, polyglutamate and polyvinyl sulfonate.

U.S. Pat. No. 5,057,597 discloses a method for the polycondensation of aspartic acid to produce polyaspartic acid by heating the aspartic acid in a fluidized bed reactor to 221° C. for a period of 3-6 hours in a nitrogen atmosphere followed by conventional alkaline hydrolysis.

Kovacs et al. (J. Org. Chem., 25 1084 [1961]) prepared polyaspartic acid by heating aspartic acid to 200° C. in vacuo for a period of 120 hours or in boiling tetralin over a period of 100 hours followed by alkaline hydrolysis. Kovacs et al, showed that the intermediate formed in the thermal polymerization of aspartic acid was polysuccinimide.

U.S. Pat. No. 3,856,380 discloses the preparation of derivatives of polyaspartic acid by reaction with a primary or secondary amine is reacted with polysuccinimide in a solvent such as dimethylformamide, diethylformamide or dimethylacetamide, followed by alkaline hydrolysis.

In a co-pending application, Ser. No. 07/882,919, incorporated herein by reference, a method of production of polyaspartic acid is disclosed in which maleic acid and ammonia are heated to 160°-300° C. followed by hydrolysis with a hydroxide.

The prior art does not disclose the synthesis of the high molecular weight copolymers of polyaspartic acid or the high molecular weight copolymers of polysuccinimide of this invention.

SUMMARY OF THE INVENTION

High molecular weight copolymers of polysuccinimide were prepared by reacting maleic acid, ammonia and a polyamine at temperatures greater than 120° C. High molecular weight copolymers of polyaspartic acid were prepared by hydrolyzing the polysuccinimide polymers with a hydroxide.

One object of this invention is to provide a means of preparing copolymers of polysuccinimide. A further object of this invention is to provide a means of preparing copolymers of polyaspartic acid. Yet another object of this invention is to provide novel compositions which are useful for the inhibition of salt deposition, especially bivalent metal salts, whether in water treatment, detergent addition, oral health care or cosmetic formulation. Yet another object of this invention is to provide novel compositions which may be further reacted to provide cosmetically useful compounds.

DETAILED DESCRIPTION OF THE EMBODIMENTS

Higher molecular weight copolymers of polyaspartic acid which are suitable for the inhibition of scale deposition may be obtained by reacting maleic acid and ammonia in a stoichiometric excess, with a compounds having 2 or more primary or secondary amine groups per molecule, at 120°-350° C., preferably 180°-300° C., and then converting the copolymer of polysuccinimide formed to a salt of a copolymer of polyaspartic acid by hydrolysis with a hydroxide. The reaction is carried out first by the addition of water to maleic anhydride, thus forming maleic acid, or to maleic acid itself, followed by addition of the appropriate amount of ammonia in the form of gaseous ammonia or as its aqueous solution. At this point, the polyamine is added. This solution is then heated to remove water. As water is removed, the mixture becomes a solid and then a melt of the mixture is formed. Water removal continues as the reaction proceeds and the temperature is brought to 120°-300° C. When the theoretical quantity of water formed in the production of the copolymer of polysuccinimide has been removed, which, depending on the temperature, may occur in even less than 5 minutes, the reaction mixture is allowed to cool. Typically, it may take up to 8 hours at 120° C., whereas it may take less than 5 minutes at 300° C. The copolymer of polysuccinimide formed can be used to make other novel and useful products by reactions such as those described in U.S. Pat. No. 4,363,797, wherein useful derivatives for cosmetic use are described or can be hydrolyzed with metal hydroxides or ammonium hydroxide to provide the appropriate salt of polyaspartic acid. The hydroxides useful in converting the copolymers of polysuccinimide formed above to copolymers of polyaspartic acid include the alkali and alkaline earth metal hydroxides and ammonium hydroxide, and other metal hydroxides, examples of which as their cations are $Na^+$, $K^+$, $Mg^+$, $Li^+$, $Ca^{++}$, $Zn^{++}$, $Ba^{++}$, $Co^{++}$, $Fe^{++}$, $Fe^{+++}$, and $NH_4^+$. Solutions of the salts of the copolymers of polyaspartic acid formed in this manner have the same scale inhibition performance and molecular weight range as do the polymers formed by the thermal polymerization of aspartic acid itself. Further manipulation to remove the water or the salts can be carried out to provide water free powders of the salts or the free acid.

Any polyamine may be used to produce these copolymers which has at least two or more primary or secondary amines available for reaction. Preferred polyamines have at least two primary amine groups. Also preferred are polyamines having at least one primary amine and the additional amine groups consist of at least one primary or secondary amine. Suitable polyamines include polyoxyalkyleneamines, polyoxyalkylenediamines or polyoxyalkylenetriamines, melamine, alkyldiamines or alkyltriamines, diethyl triamine, ethylene diamine, and hexanediamine.

The copolymers of polyaspartic acid provided by the present invention are advantageous for inhibition of scale deposition, especially where an increased molecular weight is desirable to provide appropriate biodegradability and retention on surfaces for preventing salt deposition whether in water treatment, detergent additive, oral health care or cosmetic formulation.

These compounds may be used as additives to detergents, to cosmetics and hair treating compositions and to tooth paste. Although the exact mechanism of action of these compounds is not known, it is likely that these high molecular weight copolymers interfere with the crystal structure of salt deposits. Such interference either prevents the deposit of the salt or causes the formation of a soft crystal deposit which is easily removed by water action.

EXAMPLE 1.

Thermal Co-Polymerization of mono-Ammonium Maleate with amines

In each case the following procedure was carried out with the indicated amine. A slurry of 19.6 g (0.2 mole) maleic anhydride was dissolved in 40 ml water at 80°-95° C. and stirred for 30 minutes while allowing the mixture to cool to 25° C. To this solution at 25° C. was added 30 g of 30% aqueous solution of ammonium hydroxide (0.22 mol $NH_3$). After thorough mixing, the indicated amine was added in the quantity noted. This solution was evaporated to dryness over a period of 30 minutes. The solid was then heated at 200°-230° C. for 5 minutes, removed from the heat, allowed to cool and broken up with a spatula. The solid was then heated at 235°-245° C. for 10 minutes, removed from the heat, allowed to cool and broken up with a spatula. Finally, the solid was heated at 235°-245° C. for 10-15 minutes, removed from the heat and allowed to cool to room temperature. The resulting water insoluble polymer was slurried in 40.0 ml of water and a solution of 7.6 g of sodium hydroxide in 12 ml of water was added over 5 minutes. The solution was stirred for 10-20 minutes to give a clear red-brown solution, pH 10-11.0. JEFFAMINE is a trademark of Texaco Chemical Co. for its amines and these amines are defined as follows:

JEFFAMINE T403, Mol. wt. 440, is a triamine made from trimethylolpropane which has been chain extended with propylene oxide and end-capped with primary amines.

JEFFAMINE EDR 148, mol. wt. 148, is a diamine made from triethylene glycol end capped with primary amines.

JEFFAMINE ED 600, mol. wt. 600, is a linear diamine made from a copolymer having approximately 13-14 oxyethylene units and 3-4 oxypropylene units which are endcapped with primary amines.

The copolymer of sodium polyaspartate was tested for inhibition of calcium carbonate precipitation by the calcium drift assay. In this assay a supersaturated solution of calcium carbonate is formed by adding 0.3 ml of a sodium carbonate solution (0.25M $NaHCO_3$+0.25M $Na_2CO_3$) to 29.1 ml of 0.55M NaCl and 0.01M KCl containing 0.15 ml of 1.0M $CaCl_2$ and 1.7 ppm of the material to be tested. The reaction is initiated by adjusting the pH to 7.5-8.5 by titration with 1N NaOH and addition of the material to be tested for inhibition of $CaCO_3$ precipitation at a level of 1.7 ppm. At three minutes, the reaction is seeded by the addition of 10 mg of $CaCO_3$ and the pH is recorded. The decrease in pH is directly correlated to the amount of $CaCO_3$ that precipitates. Better inhibitors show lower changes in pH. The effectiveness of the inhibition is compared to that of sodium polyacrylate, used commercially for the purpose of preventing scale formation.

Table 1 shows the molecular weight measurements, which are given as the time in minutes for the elution of the maximum peak height upon gel permeation chromatography (GPC) of 0.1 to 0.5 mg of each sample dissolved in 8 ml of the aqueous mobile phase. The GPC conditions were: column 1 cm×17.5 cm (15 ml vol), Sephadex G50; aqueous phase of 0.02M $Na_2HPO_4/H_3PO_4$ adjusted to pH 7.0; flow rate of 0.5 ml/min at 25° C.; detected by UV at 240 nm. The molecular weight standards were aprotinin, 6500 m.w., which eluted at 29 min and poly(sodium L-aspartate), 15,000 m.w. which eluted at 17 minutes.

Table 1 shows the results of these tests with the materials prepared by the method of this Example. The $CaCO_3$ drift values are calculated by subtracting the pH recorded at 20 minutes from the pH recorded at 3 minutes. The yield given is that of polysuccinimide.

TABLE 1

| Sample | Amine Added | Type | Weight of amine (g) | (moles) | Yield (g) | CaCO₃ Drift (pH units) | mol. wt. peak (min) |
|---|---|---|---|---|---|---|---|
| none | | | | | | 0.95 | |
| 384-2 | none | | | | 19.5 | 0.29 | 20.5 |
| 5000 mol. wt. polyacrylate | | | | | | 0.10 | |
| 2000 mol. wt. polyacrylate | | | | | | 0.24 | |
| 375-2 | diethylene triamine | diamine | 0.5 | .0048 | 20.3 | 0.21 | 20.6 |
| 375-4 | diethylene triamine | diamine | 1.5 | .0014 | 20.7 | 0.22 | 16 |
| 375-6 | diethylene triamine | diamine | 2.5 | .0024 | 21.2 | 0.21 | 16 |
| 367-2 | JEFFAMINE T-403 | triamine | 1.44 | .003 | 21.4 | 0.31 | 15.5 |
| 367-8 | JEFFAMINE T-403 | triamine | 2.1 | .0048 | 21.3 | 0.27 | 15 |
| 367-6 | JEFFAMINE T-403 | triamine | 2.88 | .006 | 21.2 | gelled | |
| 377-2 | melamine | triamine | 0.6 | .0048 | 20.0 | 0.31 | 24.5 |
| 374-2 | JEFFAMINE EDR 148 | diamine | 1.06 | .007 | 20.3 | 0.20 | 15.5 |
| 374-4 | JEFFAMINE EDR 148 | diamine | 3.18 | .021 | 22.1 | gelled | |
| 381-2 | JEFFAMINE ED600 | diamine | 4.3 | .007 | 23.3 | 0.25 | 16 |
| 382-2 | ethylene diamine | diamine | 0.43 | .007 | 19.7 | 0.27 | 22 |
| 382-4 | ethylene diamine | diamine | 1.29 | .022 | 20.1 | .26 | 18 |
| 382-6 | ethylene diamine | diamine | 2.15 | .0358 | 20.9 | 0.36 | 20 |
| 383-2 | ethylene diamine | diamine | 3.0 | .05 | 21.6 | 0.38 | 16.5 |
| 392-2 | hexanediamine | diamine | 1.6 | .014 | 20.9 | 0.42 | 13.9 |

EXAMPLE 2

Thermal Co-Polymerization of di-Ammonium Maleate with amines

In each case the following procedure was carried out with the indicated amine. A slurry of 23.2 g (0.2 mole) maleic acid was dissolved in 40 ml water at 80°-95° C. and stirred for 30 minutes while allowing the mixture to cool to 25° C. To this solution at 25° C. was added 60 g of 30% aqueous solution of ammonium hydroxide (0.44 mol NH₃). After thorough mixing, the indicated amine was added in the quantity noted. This solution was evaporated to dryness over a period of 30 minutes. The solid was then heated at 200°-230° C. for 5 minutes, removed from the heat, allowed to cool and broken up with a spatula. The solid was then heated at 235°-245° C. for 10 minutes, removed from the heat, allowed to cool and broken up with a spatula. Finally, the solid was heated at 235°-245° C. for 10-15 minutes, removed from the heat and allowed to cool to room temperature. The resulting water insoluble polymer was slurried in 40.0 ml of water and a solution of 7.6 g of sodium hydroxide in 12 ml of water was added over 5 minutes. The solution was stirred for 10-20 minutes to give a clear red-brown solution, pH 10-11.0 was formed. The results of the resulting polymers were tested for calcium carbonate precipitation and molecular weight as in Example 1.

TABLE 2

| Sample | Amine Added | Type | Weight of amine (g) | (moles) | Yield (g) | CaCO₃ Drift (pH units) | mol. wt. peak (min) |
|---|---|---|---|---|---|---|---|
| none | | | | | | 0.95 | |
| 384-2 | none | | | | 19.5 | 0.29 | 20.5 |
| 5000 mol. wt. polyacrylate | | | | | | 0.10 | |
| 2000 mol. wt. polyacrylate | | | | | | 0.24 | |
| 394-2 | diethylene triamine | diamine | 0.5 | .0048 | 19.6 | 0.33 | 21 |

EXAMPLE 3

Reaction of aspartic acid with amines

In each case the following procedure was carried out with the indicated amine. A slurry of 26.6 g (0.2 mole) aspartic acid was dissolved in 40 ml water. To this solution at 25° C. was added the indicated amine in the quantity noted. This solution was evaporated to dryness over a period of 30 minutes. The solid was then heated at 235°-245° C. for 30 minutes, removed from the heat, allowed to cool and broken up with a spatula. The solid was then heated at 235°-245° C. for 30 minutes, removed from the heat, allowed to cool and broken up with a spatula. Finally, the solid was heated at 235°-245° C. for 30 minutes, removed from the heat and allowed to cool to room temperature. The resulting water insoluble polymer was slurried in 40.0 ml of water and a solution of 7.6 g of sodium hydroxide in 12 ml of water was added over 5 minutes. The solution was stirred for 10-20 minutes to give a clear reddish-brown solution, pH 10-11.0 was formed. The results of the tests described in Example 1 for these materials are given in Table 3.

TABLE 2

| Sample | Amine Added | Type | Weight of amine (g) | (moles) | Yield (g) | CaCO$_3$ Drift (pH units) | mol. wt. peak (min) |
| --- | --- | --- | --- | --- | --- | --- | --- |
| none | | | | | | 0.95 | |
| 398-6 | none | | | | 19.5 | 0.21 | 19 |
| 5000 mol. wt. polyacrylate | | | | | | 0.10 | |
| 2000 mol. wt. polyacrylate | | | | | | 0.24 | |
| 398-4 | diethylenetriamine | diamine | .1 | .001 | 19.5 | 0.21 | 19 |

It will be apparent to those skilled in the art that the examples and embodiments described herein are by way of illustration and not of limitation, and that other examples may be utilized without departing from the spirit and scope of the present invention, as set forth in the appended claims.

I claim:

1. A salt produced by polymerizing (1) maleic acid, (2) ammonia and (3) a polyamine having two or more primary or secondary amine groups per molecule to a temperature greater than 120° C., to produce a crosslinked polymer, adding a metal hydroxide or ammonium hydroxide to the crosslinked polymer to produce a salt of said polymer.

2. The salt of claim 1 wherein the polyamine has at least one primary amine and the additional amine groups consist of at least one primary or secondary amine.

3. The salt of claim 1 wherein the polyamine is selected from the group consisting of polyoxyalkyleneamines, polyoxyalkylenediamines, polyoxyalkylenetriamines, alkyldiamines, alkyltriamines, and melamine.

4. The salt of claim 1 wherein the polyamine is selected from the group consisting of diethylene triamine, ethylene diamine, and hexanediamine.

* * * * *

UNITED STATES PATENT AND TRADEMARK OFFICE
CERTIFICATE OF CORRECTION

PATENT : 5,286,810
DATED : February 15, 1994
INVENTOR(S) : Louis L. Wood

It is certified that error appears in the above-identified patent and that said Letters Patent is hereby corrected as shown below:

On the title page, and column 1, line 3
Item [54] Title "Polyamind" should read —Polyamine—

Signed and Sealed this

Twenty-fifth Day of October, 1994

Attest:

BRUCE LEHMAN

Attesting Officer     Commissioner of Patents and Trademarks